United States Patent [19]
Avery

[11] Patent Number: 4,476,249
[45] Date of Patent: Oct. 9, 1984

[54] LOW COST METHOD FOR PRODUCING METHANOL UTILIZING OTEC PLANTSHIPS

[75] Inventor: William H. Avery, Silver Spring, Md.

[73] Assignee: The Johns Hopkins University, Baltimore, Md.

[21] Appl. No.: 502,291

[22] Filed: Jun. 8, 1983

Related U.S. Application Data

[63] Continuation-in-part of Ser. No. 384,329, Jun. 2, 1982, abandoned.

[51] Int. Cl.³ .......................... C07C 29/15; C07C 1/20
[52] U.S. Cl. ................................. 518/703; 204/129; 60/641.7; 518/702; 518/728
[58] Field of Search ................ 204/129; 518/702, 728, 518/703; 60/641.6, 641.7

[56] References Cited

U.S. PATENT DOCUMENTS

| | | | |
|---|---|---|---|
| 4,138,442 | 2/1979 | Chang | 518/702 |
| 4,158,637 | 6/1979 | Jones | 518/702 |
| 4,197,421 | 4/1980 | Steinberg | 518/702 |
| 4,282,187 | 8/1981 | Corbutt et al. | 518/702 |

Primary Examiner—John F. Niebling
Attorney, Agent, or Firm—Robert E. Archibald; H. Donald Nelson

[57] ABSTRACT

Method for producing low cost methanol. A source of carbon is provided to an OTEC plant or plantship which is processed to produce carbon monoxide which is reacted with hydrogen to produce methanol. The oxygen and hydrogen are obtained from the electrolysis of water with the required energy supplied by ocean thermal energy conversion.

10 Claims, 5 Drawing Figures

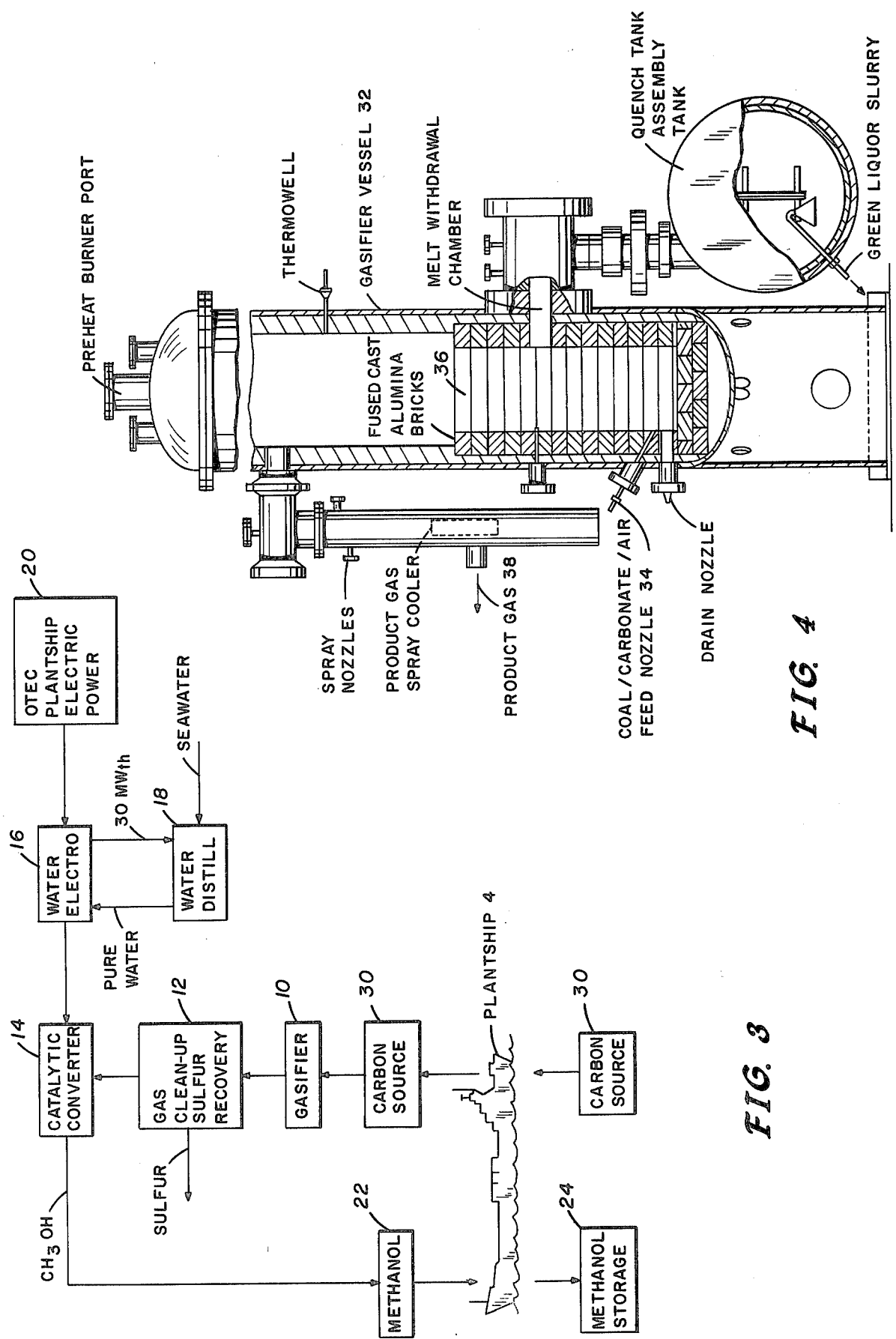

4,476,249

LOW COST METHOD FOR PRODUCING METHANOL UTILIZING OTEC PLANTSHIPS

STATEMENT OF GOVERNMENT INTEREST

The Government has rights in this invention pursuant to Contract N00024-78-C5384 awarded by the Department of the Navy.

This application is a continuation-in-part of application Ser. No. 384,329, filed 6/2/82, now abandoned.

BACKGROUND OF THE INVENTION

The present invention relates to a low cost method for producing methanol from coal or other source of carbon utilizing an ocean thermal energy conversion (OTEC) plantship. More specifically, the present invention relates to a low cost method for producing methanol and other hydrocarbon fuels utilizing carbon-free sources of hydrogen and pure oxygen available from water electrolysis on an OTEC plantship. The unique advantages of the present invention are that the low cost hydrogen and oxygen which can be produced by use of inexhaustible solar energy absorbed in the surface waters of the tropical oceans allow methanol and derivative hydrocarbon fuels to be produced at minimum cost and the method of producing the methanol does not produce carbon dioxide as a by-product.

The world is entering into an era of increasing shortages of natural sources of energy. Conservative estimates indicate that if in one hundred years the world per capita energy demand is only two-thirds of current U.S. per capita consumption and if population-control techniques are successful, the world will require 3000 quads ($3 \times 10^{18}$ BTU) of energy per year as compared with current world consumption of approximately 300 quads per year. This is a ten-fold increase in one hundred years.

It is apparent that (1) the demand for transportation fuels will not be met by crude oil and natural gas resources, and (2) it will be necessary to develop a worldwide synfuel industry utilizing coal as the primary source of carbon. However, two major problems are associated with the establishment of a coal-based synthetic fuel industry to meet the world future demands. The first problem is that $CO_2$ levels in the atmosphere are rising at a rate that is linearly proportional to the combustion of carbon. A substantial body of scientific opinion predicts that, if the concentration of atmospheric $CO_2$ continues to increase at this rate, deleterious climatic changes could occur as early as the year 2030. The second and more immediate problem is the deficiency of hydrogen in coal. In simplified terms, the hydrogen-carbon ratio of good synthetic fuel is approximately 2.0 whereas the hydrogen-carbon ratio in the average coal deposit is approximately 0.8. Because of the lack of hydrogen the inefficient synfuel process throws away excess carbon in the form of $CO_2$ and coke. As can be appreciated, the thrown away $CO_2$ and the thrown away coke is a waste of valuable carbon. In the more efficient Fischer-Tropsch process, hydrogen is obtained from the water molecule by an exchange process ($2C + 2H_2O \rightarrow CH_4 + CO_2$). This also aggravates the problem of atmospheric $CO_2$ and of course is also a waste of valuable carbon.

As can be appreciated, the solution to the problem of adding excess carbon to the atmosphere in the form of $CO_2$ is to have a major source of carbon free hydrogen.

One of the most attractive synfuels is methanol because it can be used directly as a motor fuel in internal combustion engines or it may be converted into hydrocarbon fuel. For example, the Mobil process involving dehydration of methanol can be used to produce hydrocarbon fuel at over 95% efficiency (Mobil Methanol to Gasoline Process, David Liederman et al, 15th IECEC Conf., Seattle, Wash., Aug. 18–22, 1980). Methanol is also a preferred fuel for fuel cells of the molten carbonate type, in which over 60% conversion of the heating value (HHV) of the fuel to electric power has been demonstrated.

Methanol is conventionally made at the present time from natural gas by a process which involves the following steps:

|  | $-\Delta H$ kcal/gmol |
|---|---|
| (1) $CH_4 + H_2O \rightarrow CO + 3H_2$ | $-49.3$ |
| (2) $CO + 2H_2 \rightarrow CH_3OH$ | $21.6$ |
| (3) $CH_4 + 2O_2 \rightarrow CO_2 + 2H_2O$ | $191.8$ |

The first reaction, as shown, is endothermic and reaction (3) is, therefore, necessary to supply heat for the process. In the normal commercial process, this means that, as an example, 32,000 standard cubic feet (SCF) of natural gas may be consumed per ton of methanol produced. Because of this and the increasing cost of natural gas, considerable effort is being directed towards finding economic alternatives for preparing methanol.

The use of OTEC plantships for the production of methanol solves two major problems. First, the electrolysis of water to produce carbon-free hydrogen decreases the amount of $CO_2$ injected into the atmosphere and second, the electrolysis of water can be accomplished economically by utilizing an inexhaustible source of energy. The OTEC plantships comprise energy producing systems which exploit the difference in temperature between the surface and deep ocean waters to run a Rankine engine or the equivalent and thereby generate electric power. Regions having an average temperature differential ($\Delta T$) of 20°–25° C. are particularly attractive for OTEC plants. The highest $\Delta T$'s and the smallest seasonal variations in $\Delta T$ are noted in the tropical areas of the Pacific and Atlantic Oceans and these areas are consequently particularly attractive for OTEC plants.

OTEC plantships are ships which may be moored but usually cruise slowly in the selected tropical ocean area to generate electric power by means of a turbine generator driven via a closed Rankine cycle. Since the temperature difference which is relied upon is dependent on solar energy absorbed at the ocean surface, it is evident that OTEC plants offer an essentially inexhaustible energy source for the production of electricity. It is estimated, for example, that with 325 $MW_e$ plantships spaced at 30-mile intervals, the total electric power produced on board would be around 10 million megawatts, 40 times present U.S. electric power generation.

A further advantage of OTEC plantships is that the electric power generated thereon may be used to make various chemical products, e.g., ammonia, which may be stored aboard the ship and delivered at appropriate ports when and as desired. Typically, OTEC electric power may be used to electrolytically produce $H_2$ and $O_2$ from ocean water, the gases thus obtained being available for appropriate reactions.

Substantial effort has also been directed towards obtaining synthetic fuels ("synfuels") by pyrolysis of coal and char oxidation. One such system is that known as the char oil energy development (COED) process developed by FMC Corporation (see "Char Oil Energy Development", Vol 1, J. F. Jones et al, FMC Corp. for U.S. Dept. of Commerce, Rept. FE-1212-T-9; and "The Pyrolysis Route to Gasification", R. Tracy Eddinger, Reprint #8412-0513-2/79/0779, A. Chem. Soc.).

In the conventional COED system, bituminous coal is subjected to pyrolysis to produce oil, gas and char. The char may then be converted to liquid fuel by (1) introduction of steam and $O_2$ into a vessel containing the char where reaction occurs to form CO, $H_2$; followed by (2) reaction of the CO with $H_2$ to form methanol, the latter being subsequently dehydrated in a further step, e.g., by the Mobil process, to form gasoline $(CH_2)_n$ and water.

The conventional COED process, which is entirely land-based, requires the use of pure $O_2$, which must be supplied by an air liquefaction plant thus adding significantly to the overall cost of oxidation step (1). Additionally, overall efficiency is reduced because roughly half of the char has to be oxidized to $CO_2$ to provide heat for the reaction:

$$C + H_2O \rightarrow CO + H_2$$

which is endothermic and to provide additional $H_2$ as needed via the reaction:

$$C + 2H_2O \rightarrow CO_2 + H_2$$

which is also endothermic.

It is therefore one object of this invention to provide a method of producing methanol and derivative hydrocarbon fuels by use of inexhaustible electrical energy from the ocean for production of pure hydrogen and oxygen at minimum cost.

It is another object of this invention to provide a method of producing methanol and derivative hydrocarbon fuels utilizing a low cost source of hydrogen which does not require carbon as a feed stock.

It is a further object of this invention to provide a method of producing methanol and derivative hydrocarbon fuels without injecting waste $CO_2$ into the atmosphere.

It is still another object of this invention to provide a method of producing methanol and derivative hydrocarbon fuels by combining efficient land based procedures and efficient OTEC plantship procedures.

SUMMARY OF THE INVENTION

These and other objects, features and advantages of the present invention are accomplished by providing a source of carbon to an OTEC plantship, processing the source of carbon to produce carbon monoxide and combining the carbon monoxide with hydrogen, which is procured on board the OTEC plantship together with oxygen by the electrolysis of water to form methanol. The power required for the electrolysis is provided by ocean thermal energy conversion.

BRIEF DESCRIPTION OF THE DRAWINGS

The above and further objects and novel features of the present invention will more fully appear from the following description when the same is read in connection with the accompanying drawings. It is to be understood, however, that the drawings are for the purpose of illustration only and are not intended as a definition of the limits of the invention.

FIG. 3 is an illustration of the method of the present invention showing the use of a carbon source in the method.

FIG. 4 is a diagram of a molten salt gasifier.

DETAILED DESCRIPTION OF THE PREFERRED EMBODIMENTS

Methanol synthesis from coal requires two basic processes: (1) reaction of coal and oxygen to form CO; and (2) reaction of CO with hydrogen to form $CH_3OH$. In conventional plant designs for methanol synthesis, oxygen is produced by air liquefaction and separation which uses energy, and hydrogen by reaction of water with carbon in an endothermic process which consumes roughly half the carbon to provide the process heat. The availability of pure hydrogen and pure oxygen from water electrolysis on an OTEC plantship permits significant simplification of the methanol process equipment and twofold improvements in the output of methanol per ton of coal.

Figure 1:
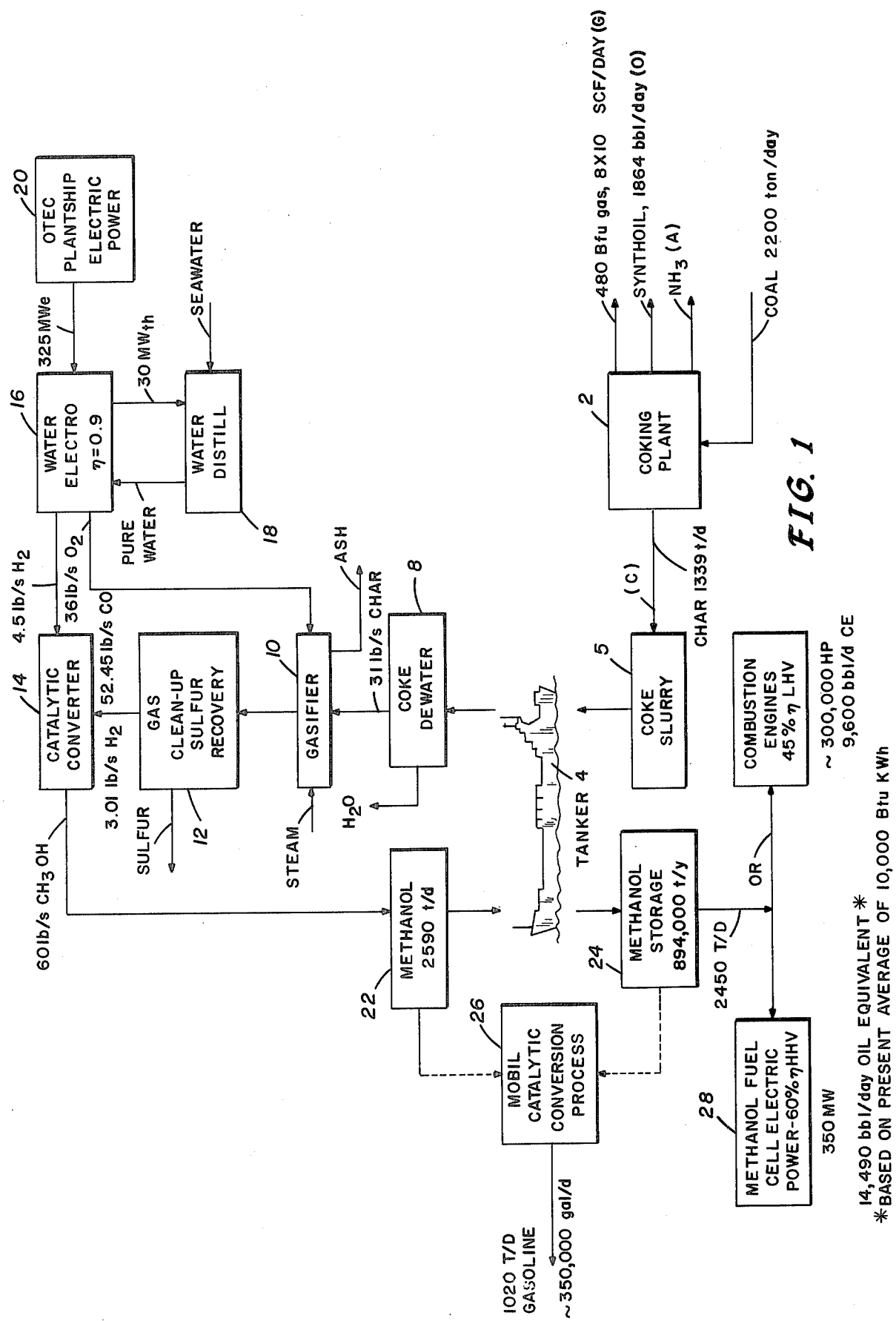
FIG. 1 illustrates the method of the present invention utilizing a coke slurry as a carbon source.

One way of carrying out the process of the present invention is shown in FIG. 1 which diagrammatically illustrates a land-based pyrolysis unit or coking plant (2) and an OTEC plantship (4).

As shown in FIG. 1, coal (e.g., bituminous coal, Pittsburgh #8 seam) is subjected to pyrolysis in the coking plant (2). This gives gas (G), oil (O), ammonia (A) and char (C). The gas, oil and ammonia products may be removed and used in any desired fashion. The char (C) is slurried in water at (5) to give a "coke slurry" which is transported to the OTEC plantship by a tanker. The plantship which houses the items 8, 10, 12, 14, 16, 18, 20 is moored offshore or preferably cruising slowly through ocean water having a $\Delta T$ between the water surface and a depth thereof of at least about 20°–25° C.

On the plantship, the slurry is dewatered as shown at (8), subjected to reaction in the gasifier (10) with steam and oxygen to form CO gas and $H_2$, the gas being processed at stage (12) to remove sulfur and other impurities. The resulting purified CO and $H_2$ gas is then catalytically converted as shown at (14) using conventional Fisher-Tropsch reaction conditions with added hydrogen obtained from the water electrolysis unit (16). This unit also provides the oxygen for the CO-forming reaction at the gasifier (10).

Pure water for the electrolysis unit (16) is obtained, as shown, by the distillation of sea water at (18) in whole or in part or by separation of water from the char slurry. Electric power (20) for the electrolysis is obtained by operation of the conventional OTEC system where, as noted earlier, the temperature difference at different water levels is used to drive a Rankine engine or the equivalent to generate electric power.

Methanol (22) produced at the converter (14) may be stored, converted into gasoline by any convenient dehydration process (e.g., the Mobil process) and/or used to generate power either/or in a fuel cell to provide electric power as shown at (24), (26) and (28), or in combustion engines (30) respectively. Estimated production values are shown at various stages in FIG. 1 based on the use of 2200 tons per day of coal. As shown, the system is estimated to be capable of producing about 2590 tons per day of methanol or 350,000 gallons per day of gasoline based on 2200 tons of coal per day.

As will be evident, the availability of the electrolytically-produced $H_2$ and $O_2$ on the OTEC plantship offers certain apparent advantages over totally land-based coal pyrolysis-char-fuel conversion procedures. The main reactions involved in (10) and (14) are:

$$C + \tfrac{1}{2}O_2 \rightarrow CO \quad (4)$$

and $$CO + 2H_2 \rightarrow CH_3OH \quad (5)$$

These are exothermic, so there is no need to burn part of the carbon to provide heat. The same is true for the conversion of $CH_3OH$ to gasoline as follows:

$$CH_3OH \rightarrow (CH_2)_n + H_2O \quad (6)$$

The excess energy may be used to generate additional CO and $H_2$ via the reaction $$C + H_2O \rightarrow CO + H_2. \quad (7)$$

(The disproportionation reaction, $2\ CO \rightarrow C + CO_2$, will also occur but is not involved in the heat balance.) Allowing some exothermicity to compensate for heat loss in the char-gasification step, the combined reactions for the production of OTEC methanol from carbon may be represented as:

| | $-\Delta H$ kcal/gmol | |
|---|---|---|
| $2.5C + H_2O + 4H_2 + \tfrac{1}{2}O_2\ 2.5 \rightarrow CH_3OH$ | 63 | (8) |

It will be apparent that specific operating conditions can be widely varied and will depend in any case on the selected designs of the carbon supply unit and OTEC plantship. The choice of conditions for the various stages, e.g., for the catalytic conversion of the CO and $H_2$ to methanol or other details of operation in either the coking plant and/or the OTEC plantship will be readily determined by those in the art and do not constitute per se a part of the present invention.

Conventional equipment may be used for the char slurry handling apparatus, transport system described in FIG. 1. The same is true for other stages of the system shown in FIG. 1. Thus, the char gasifier may be, for example, a British Gas/Lurgi moving-bed counterflow slagging design as known in the art. In such designs, char is fed downwardly through the gasifier where it is dried and devolatilized by counterflowing hot gases from the combustion zone where oxygen and stem are injected. The high temperature melts the ash which forms a molten slag pool that may be removed periodically and discharged (not shown) and exit gases which preferably are cooled before further processing. A typical exit gas composition based on the COED char gasification process, modified for OTEC-$O_2$ oxidation, may be:

| | $H_2O$ | $CO_2$ | CO | $H_2$ | $CH_4$ | $H_2S$ | Total |
|---|---|---|---|---|---|---|---|
| Vol. % | 0.84 | 1.7 | 63.2 | 33.6 | 0.7 | 0.02 | 100 |
| Wt. % | 0.78 | 4.02 | 91.0 | 3.6 | 0.6 | 0.03 | 100 |

Before the gas can be fed to methanol synthesis, all traces of sulfur (and acid gases) should be removed. This can be done by further cooling the gas and washing with methanol. Carbon dioxide may also be removed by absorption in a potassium carbonate solution in a countercurrent packed column. The $CO_2$ content of the gas is adjusted, after addition of OTEC-$H_2$, to a methanol synthesis feed range of $(H_2-CO_2)/(CO+CO_2) = 2.05$ to 2.8 by volume.

The OTEC hydrogen is mixed with the gas stream before admission to the methanol synthesis section (14) where the main reaction with CO and the following reaction:

$$CO_2 + 3H_2 = CH_3OH + H_2O$$

may be carried out over, for example, a copper catalyst at approximately 260° C. The exothermic reactions involved may be controlled by recycle gas compression and cooling exchangers where water is removed and the methanol is condensed and transferred to storage tanks.

Figure 2:
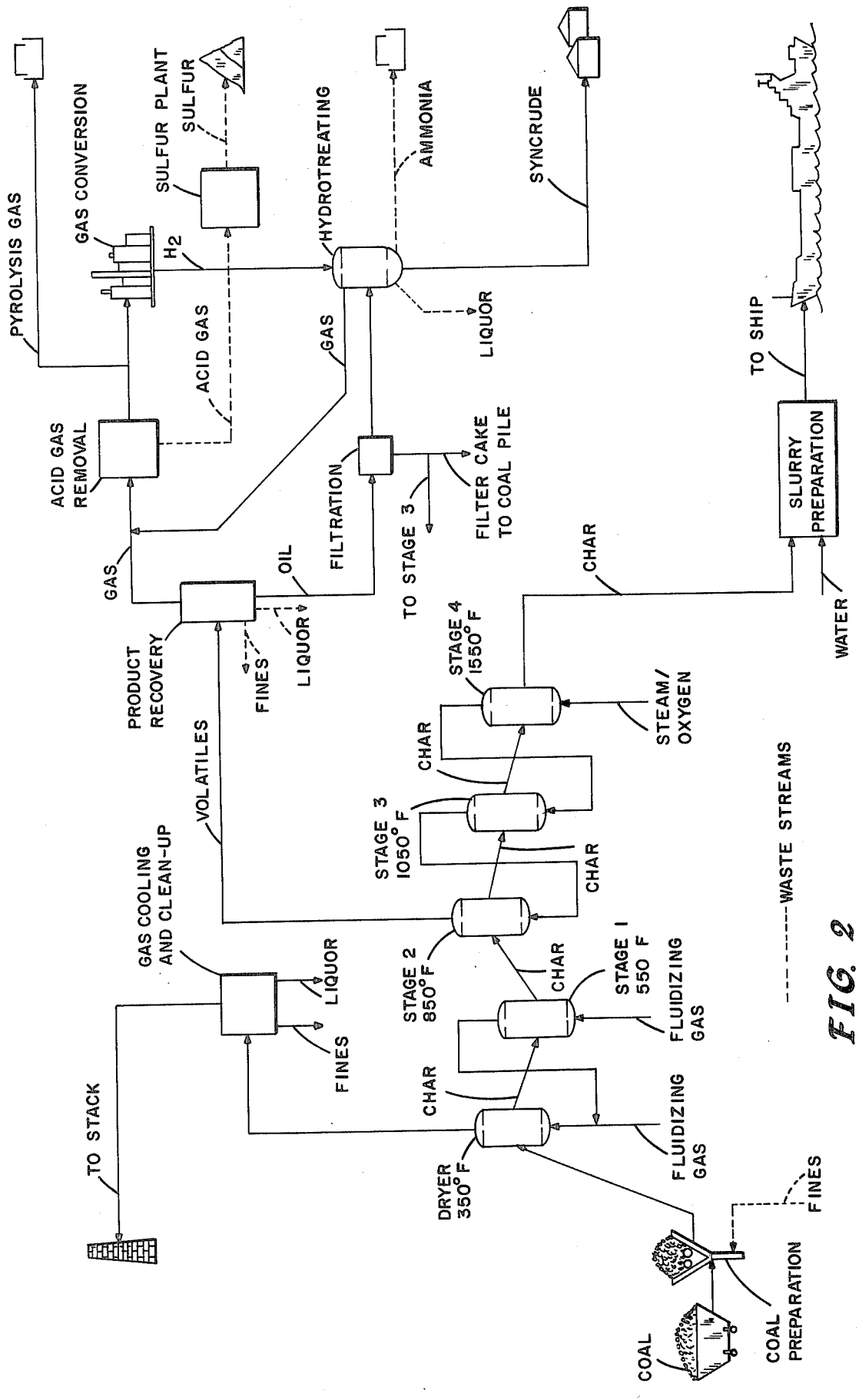
FIG. 2 is a flow diagram illustrating various operations in the pyrolysis of coal to obtain the slurry for use on the OTEC plantship.

FIG. 2 is a schematic drawing or flow sheet showing various operations involved in the pyrolysis of coal to obtain the slurry for use on the OTEC plantship according to the invention. The system shown in FIG. 2 (up to the preparation of the coke slurry) represents a conventional COED plant. In contrast to conventional COED operations, FIG. 2 shows the slurry being transported to an OTEC plantship, for processing as in FIG. 1 according to the invention rather than being subjected to gasification and methanol formation on land as in the COED system. The various operations involved in the system are appropriately indicated in FIG. 2 so that further description of these operations is not needed.

Table 1 shows the product yield (B) and char composition (C) obtainable by COED pyrolysis of bituminous coal having the composition given in (A).

TABLE I

| COED PYROLYSIS OF Bituminous Coal (Pittsburgh #8 Seam) | | |
|---|---|---|
| | Wt. % | lbs/ton coal |
| (A) Coal Composition Dry Basis | | |
| Carbon | 73.8 | 1476 |
| Hydrogen | 5.3 | 106 |
| Nitrogen | 1.2 | 24 |
| Sulfur | 4.0 | 80 |
| Oxygen | 7.5 | 150 |
| Ash | 8.3 | 166 |
| (B) Product Yield (AV) | | |
| Char | 63.3 | 1266 |
| Oil | 16.5 | 330 (0.85 bbl) |
| Gas | 8.7 | 174 (3675 SCF) |
| (C) Char Composition | | |
| Carbon | 73.3 | 928 |
| Hydrogen | 5.1 | 65 |
| Nitrogen | 1.3 | 17 |
| Sulfur | 4.6 | 58 |
| Oxygen | 6.8 | 86 |
| Ash | 8.9 | 113 |

The data in Table 1 discloses that the char produced by pyrolysis contains a significant fraction of hydrogen, oxygen and sulfur, which must be considered in the conversion of char to methanol. The sulfur should be removed as shown in FIG. 1. However, the oxygen and hydrogen can be useful in the char gasification and methanol production steps and the content thereof in the char should be taken into account in determining the amount of oxygen and hydrogen to be applied to the respective steps. Thus, for example, if it is assumed that the oxygen in the char is bonded to carbon, the 86 lb of oxygen in the 1266 lb of char will be associated with $86 \times 12/16 = 64.5$ lb of carbon. In the char oxidation, this will react with $H_2$ according to reaction (5). Thus the 86 lb of combined oxygen will consume 21.5 lb of hydrogen. The remaining 43.5 lb of hydrogen in the char will be available to react according to reaction (8) with 163 lb of carbon. The rest of the carbon in the char to be consumed is then $928-64.5-163 = 700$ lb. Therefore, to complete reaction (8), 187 lb of $H_2$ will need to be supplied from the on-board electrolysis plant. Overall then, 187 lb of OTEC electrolytic $H_2$ react with 1266 lb of char in the total process to produce 2475 lb of methanol. The ratio by weight of methanol to electrolytic hydrogen is 13.3. Therefore, 4.54 lb/s of $H_2$ should generate 60 lb/s of methanol or 2590 t/d.

To supply the OTEC plantship, it is estimated that 1339 t/d of char would be required from the land-based pyrolysis plant, and the dry coal input to the pyrolysis plant would be 2200 t/d. As shown in Table 1, the char production will be accompanied by production of 1865 bbl/d, of synthetic oil and 18 million SCF/d of 480 BTU/SCF gas. This gas may be sold or used in various ways, e.g., to provide steam and power for the pyrolysis plant. With 345 days per year operation the OTEC methanol output per plantship could be 894,000 t/y (ton per year) or 268 million gallons per year.

It will be appreciated from the foregoing that an essential aspect of the invention is the concept of using $H_2$ and $O_2$ electrolytically generated on an OTEC plantship to prepare methanol. In one embodiment, the invention contemplates combining features of a land-based coal pyrolysis process and of an OTEC plantship designed to produce $H_2$ and $O_2$ electrolytically wherein the pyrolysis extracts useful hydrocarbon liquids from coal, the resulting char is shipped as a slurry to an OTEC plantship where it is combusted with OTEC electrolytic oxygen to form methanol (and/or gasoline).

The overall process appears to offer numerous advantages over previously proposed procedures—including, for example, the effective utilization of both $O_2$ and $H_2$ of OTEC water electrolysis, and the simplification of on-land and plantship equipment. The result is a minimum cost process which offers the promise of commercially attractive production of OTEC methanol and gasoline. Thus, for example, it is estimated that the present process, combining land-based coal pyrolysis and OTEC plantship operations, will produce $2.5 \times 10^7$ BTU per ton using a recently proposed land-based process for making methanol from coal (see Grace/DOE Coal to Methanol Project-Doyle 8th Energy Technology Conference, Washington, D.C., Mar. 11, 1981).

It will be appreciated that the process as detailed above may be modified to eliminate land-based pyrolysis of coal. Thus, the pyrolysis could be carried out on board the OTEC plantship. In a more preferred alternative, however, the process may be carried out using pulverized coal or an aqueous coal slurry as the input to the OTEC plantship. This alternative would eliminate the onshore pyrolysis and its resultant production of oil and gas. However, this modification would still preserve the advantages of using OTEC-generated hydrogen and oxygen compared to land-based methanol-producing operations which require a secondary liquid oxygen plant to supply oxygen and a shift conversion section in which roughly one-half of the coal is burned to supply heat for the reaction:

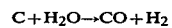

$$C + H_2O \rightarrow CO + H_2$$

FIG. 3 illustrates an embodiment of the present invention wherein other sources of carbon may be utilized to produce methanol. For example, a carbon source such as pulverized coal, indicated at (30), may be transported to the OTEC plantship. Other sources of carbon include bagasse, kelp, wood and carbonaceous waste such as plastics. Other components shown in FIG. 3 are similar to those shown in FIG. 1. Modification to individual components may be required depending upon the carbon source utilized. However, these modifications would be within the state-of-the-art and are not discussed herein.

Figure 5:
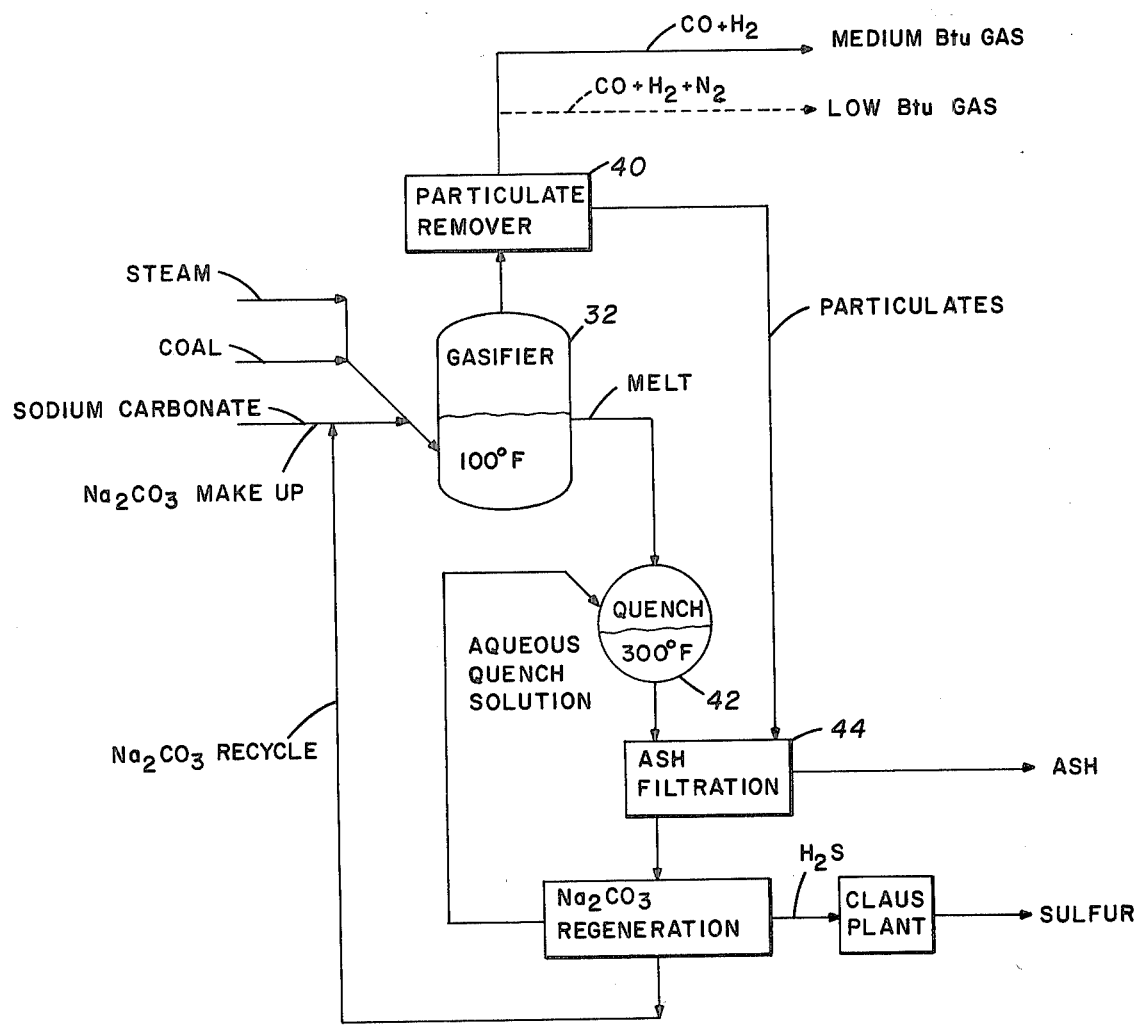
FIG. 5 is a flow diagram of the molten salt gasifier process.

Another embodiment of the present invention replaces the gasifier described above with a molten salt gasifier. An example of a molten salt gasifier is shown in FIG. 4 and is a molten carbonate gasifier (32) developed by Rockwell International Corporation. The feedstock is dry coal, ground to pass through a $\frac{1}{4}''$ mesh screen, which is pneumatically injected through a feed nozzle (34) near the bottom of a molten bed of sodium carbonate (36) which is at a temperature of 1800° F. Also injected at the same time as the coal is oxygen and steam. The reaction is rapid, assisted by the catalytic action of sodium sulfide in the melt, and the gas emerging at (38) is essentially at chemical equilibrium for the components carbon, oxygen and hydrogen. A schematic of the gasifier (32) is shown in FIG. 5. Pulverized coal, steam and sodium carbonate are input to gasifier (32) which is maintained at 1800° F. The gases are throughput a particulate remover (40) for further processing. The melt from gasifier (32) is throughput a quench, at (42), at a temperature of 300° F., then to an ash filtration unit (44) and the sodium carbonate is regenerated and the sulfur removed. The sulfur in the input coal reacts with the melt to form sodium sulfide which provides a catalytic action in the melt.

What I claim is:

1. method of producing low cost methanol from coal aboard an OTEC plant or plantship comprising the steps of:
   providing a source of carbon to an OTEC plant or plantship;
   obtaining carbon free hydrogen and electrolytic oxygen aboard said OTEC plant or plantship by the electrolysis of water using OTEC electric power;
   processing said source of carbon with said electrolytic oxygen to obtain carbon monoxide;
   reacting said carbon monoxide with said free hydrogen to obtain methanol.

2. A method, as recited in claim 1, wherein the step of providing a source of carbon to an OTEC plant or plantship is accomplished by:
   the pyrolysis of coal to obtain char; and
   transporting said char to said OTEC plant or plantship.

3. A method, as recited in claim 2, wherein the step of transporting said char to said OTEC plant or plantship is accomplished by forming said char in an aqueous slurry.

4. A method, as recited in claim 3, furtner comprising the step of dewatering said aqueous slurry on-board said OTEC plant or plantship.

5. A method, as recited in claim 4, wherein the step of processing said source of carbon to obtain carbon monoxide is accomplished by processing said source of carbon in a gasifier.

6. A method, as recited in claim 1, wherein the step of providing a source of carbon to an OTEC plant or plantship is accomplished by:
   pulverizing said coal; and
   transporting said pulverized coal to said OTEC plant or plantship.

7. A method, as recited in claim 6, wherein the step of processing said source of carbon to obtain carbon monoxide is accomplished by processing said pulverized coal in a molten salt gasifier.

8. A method, as recited in claim 5 or 7, further comprising the steps of:
   combining said oxygen with said carbon to form carbon monoxide; and
   combining said hydrogen with said carbon monoxide to obtain said methanol.

9. A method, as recited in claim 8, further comprising the steps of:
   generating electric power aboard said OTEC plantship by ocean thermal energy conversion; and
   powering said electrolysis with said generated electric power.

10. A method, as recited in claim 1, further comprising the step of transporting said methanol from said OTEC plantship.

* * * * *